United States Patent
Rosendahl et al.

(10) Patent No.: US 8,921,587 B2
(45) Date of Patent: Dec. 30, 2014

(54) PROCESS FOR PRODUCING A CATALYST FOR THE OXIDATION OF ETHYLENE TO ETHYLENE OXIDE

(75) Inventors: Tobias Rosendahl, Mannheim (DE); Torsten Mäurer, Ludwigshafen (DE); Cornelia Katharina Dobner, Ludwigshafen (DE)

(73) Assignee: BASF SE (DE)

( * ) Notice: Subject to any disclaimer, the term of this patent is extended or adjusted under 35 U.S.C. 154(b) by 0 days.

(21) Appl. No.: 13/446,197

(22) Filed: Apr. 13, 2012

(65) Prior Publication Data

US 2012/0264954 A1    Oct. 18, 2012

(51) Int. Cl.
| | | |
|---|---|---|
| *C07D 301/03* | (2006.01) |
| *B01J 27/02* | (2006.01) |
| *B01J 27/13* | (2006.01) |
| *B01J 23/48* | (2006.01) |
| *B01J 37/02* | (2006.01) |
| *B01J 35/02* | (2006.01) |
| *B01J 23/68* | (2006.01) |
| *C07D 301/10* | (2006.01) |
| *B01J 35/04* | (2006.01) |
| *B01J 35/10* | (2006.01) |
| *B01J 21/04* | (2006.01) |

(52) U.S. Cl.
CPC ........... *C07D 301/10* (2013.01); *B01J 35/1066* (2013.01); *B01J 37/0201* (2013.01); *B01J 35/109* (2013.01); *B01J 35/023* (2013.01); *B01J 23/688* (2013.01); *B01J 35/1076* (2013.01); *B01J 37/0213* (2013.01); *B01J 35/04* (2013.01); *B01J 21/04* (2013.01); *B01J 35/1009* (2013.01)
USPC ............ 549/536; 502/216; 502/347; 502/330

(58) Field of Classification Search
CPC ............ B01J 23/78; B01J 23/52; B01J 23/58; B01J 23/66; B01J 23/688; B01J 23/50; B01J 35/109; B01J 35/04; B01J 37/0201; B01J 35/1009; B01J 35/023; B01J 37/0213; B01J 21/04; B01J 35/1066; B01J 35/1076; C07C 2523/04; C07C 2523/745; C07D 301/10; C07D 303/04
USPC ........................... 502/347, 330, 216; 549/536
See application file for complete search history.

(56) References Cited

U.S. PATENT DOCUMENTS

| | | | | |
|---|---|---|---|---|
| 5,102,848 | A * | 4/1992 | Soo et al. ...................... 502/218 |
| 2004/0260103 | A1 | 12/2004 | Matusz et al. |
| 2008/0015393 | A1 | 1/2008 | Matusz et al. |

FOREIGN PATENT DOCUMENTS

| | | |
|---|---|---|
| CN | 1467028 A | 1/2004 |
| DE | 2300512 A1 | 7/1973 |
| DE | 2454972 A1 | 6/1975 |
| DE | 2521906 A1 | 12/1975 |
| DE | 2753359 A1 | 6/1979 |
| DE | 3150205 A1 | 8/1982 |
| DE | 3321895 A1 | 12/1983 |
| DE | 3414717 A1 | 10/1985 |
| DE | 2560684 C2 | 10/1989 |
| EP | 0011356 A1 | 5/1980 |
| EP | 14457 A2 | 8/1980 |
| EP | 0082609 A1 | 6/1983 |
| EP | 0085237 A1 | 8/1983 |
| EP | 0172565 A2 | 2/1986 |
| EP | 0229465 A1 | 7/1987 |
| EP | 0266015 A1 | 5/1988 |
| EP | 0339748 A2 | 11/1989 |
| EP | 0357293 A1 | 3/1990 |
| EP | 384312 A1 | 8/1990 |
| EP | 0496386 A1 | 7/1992 |
| EP | 1613428 A2 | 1/2006 |
| WO | WO-2006102189 A1 | 9/2006 |

OTHER PUBLICATIONS

Ullmann's Encyclopedia of Industrial Chemistry, 5th edition, vol. A-10, pp. 117-135, 123-125, VCH-Verlagsge-sellschaft, Weinheim 1987.
Notification of Transmittal of the International Search Report and the Written Opinion of the International Searching Authority from PCT/EB2012/051833 dated Sep. 20, 2012.

* cited by examiner

*Primary Examiner* — Anthony J Zimmer
*Assistant Examiner* — Haytham Soliman
(74) *Attorney, Agent, or Firm* — Drinker Biddle & Reath LLP

(57) ABSTRACT

The present invention relates to a shaped catalyst body for preparing ethylene oxide, which comprises at least silver and rhenium applied to an alumina support, and also to a process for producing it, wherein the alumina support has the geometry of a hollow cylinder and the shaped catalyst body has a rhenium content $C_R$ and $C_R$/ppm by weight, based on the wall thickness of the hollow cylinder $d_W$ in mm, and calculated as element, in the range $120 \leq C_R/d_W \leq 200$.

19 Claims, No Drawings

PROCESS FOR PRODUCING A CATALYST FOR THE OXIDATION OF ETHYLENE TO ETHYLENE OXIDE

CROSS-REFERENCE TO RELATED APPLICATIONS

This application claims benefit (under 35 USC 119(e)) of U.S. Provisional Application 61/475,240, filed Apr. 14, 2011, which is incorporated by reference.

BACKGROUND OF THE INVENTION

The present invention relates to a shaped catalyst body for preparing ethylene oxide, which comprises at least silver and rhenium applied to an alumina support, wherein the alumina support has the geometry of a hollow cylinder and the shaped catalyst body has a rhenium content $C_R$ and $C_R$/ppm by weight, based on the wall thickness of the hollow cylinder $d_W$ in mm, in the range $120 \leq C_R/d_W \leq 200$. The invention further relates to a process for producing this shaped body and the use of this shaped body as catalyst for converting ethylene into ethylene oxide.

Ethylene oxide is an important basic chemical and in industry is frequently prepared by direct oxidation of ethylene by means of oxygen in the presence of silver-comprising catalysts. Supported alumina catalysts in which the catalytically active metallic silver has been applied by means of a suitable process to an alumina support are usually used. As alumina support material, it is basically possible to use various porous materials such as activated carbon, titania, zirconia, silica, alumina or ceramic compositions or mixtures of these materials. Particularly preferred alumina supports are based on alpha-alumina. As examples of the direct oxidation of ethylene, mention may be made of DE-A-2300512, DE-A-2521906, EP-A-0014457, DE-A-2454972, EP-A-0172565, EP-A-0357293, EP-A-0266015, EP-A-0011356, EP-A-0085237, DE-C2-2560684 or DE-A-2753359.

To improve the activity and/or the selectivity of the catalysts in the oxidation of ethylene to ethylene oxide, promoters are also applied in addition to the active material silver to the alumina support. Mention may be made by way of example of alkali metal and/or alkaline earth metal compounds, tungsten, molybdenum or rhenium, with rhenium being a particularly preferred promoter. For the purposes of the present invention, the term "selectivity" refers to the percentage of the ethylene used in the process which is converted into ethylene oxide in the oxidation. As regards the activity of the catalyst, the activity of the catalyst is higher, the lower the temperature required to achieve a given concentration of ethylene oxide at the reactor outlet under otherwise constant reaction conditions.

To influence the activity and/or the selectivity of such catalysts, various measures are disclosed in the documents of the prior art.

Thus, US 2004/0260103 A1 describes influencing the activity of a catalyst by changing the geometry of the catalyst. In this context, catalysts in the form of hollow cylinders having a ratio of external diameter to wall thickness in the range from 0.3 to 2 mm are said to be advantageous, with the wall thickness being made larger than in the case of hollow cylinders conventionally used. Increasing the rhenium concentration when increasing the wall thickness is not described.

EP 1 613 428 B1 describes a process for converting ethylene into ethylene oxide in the presence of a catalyst comprising rhenium in an amount of not more than 1.5 mmol/kg, based on the total weight of the catalyst, and not more than 0.0015 mmol/m², based on the BET surface area of the support. The low initial selectivity in the epoxidation reaction resulting from the small amount of rhenium is compensated by increasing the temperature stepwise during the epoxidation reaction. According to EP 1 613 428 B1, the catalysts described there are supposed to have a longer lifetime compared to those having a higher rhenium content.

It was an object of the present invention to provide more advantageous catalysts for the oxidation of ethylene to ethylene oxide.

It has surprisingly been found that shaped catalyst bodies, in which at least silver and rhenium have been applied to an alumina support having the geometry of a hollow cylinder and which have a rhenium content $C_R$ such that $C_R$/ppm by weight, based on the wall thickness of the hollow cylinder $d_W$ in mm, is in the range $120 \leq C_R/d_W \leq 200$, display advantageous selectivities and/or activities in the conversion of ethylene into ethylene oxide. Altering the geometry of a catalyst thus surprisingly gives, by modifying the rhenium concentration (increasing the concentration when increasing the wall thickness) in an otherwise identical composition, catalysts having particularly advantageous catalytic properties in the oxidation of ethylene to ethylene oxide.

The present invention therefore also provides a shaped catalyst body for preparing ethylene oxide, which comprises at least silver and rhenium applied to an alumina support, wherein the alumina support has the geometry of a hollow cylinder and the shaped catalyst body has a rhenium content $C_R$ and $C_R$/ppm by weight, based on the wall thickness of the hollow cylinder $d_W$ in mm, in the range $120 \leq C_R/d_W \leq 200$.

The present invention likewise provides a process for producing a shaped catalyst body and a shaped catalyst body which can be produced or has been produced by this process, where the process comprises:

(a) providing an alumina support which has the geometry of a hollow cylinder,
(b) applying silver and rhenium to the alumina support, with rhenium being applied in an amount of $C_R$/ppm by weight, based on the wall thickness of the hollow cylinder $d_W$ in mm and calculated as element which is in the range $120 \leq C_R/d_w \leq 200$, to the alumina support.

Support Geometry

According to the present invention, the alumina support has the shape of a hollow cylinder. The precise dimensions of this hollow cylinder are generally of minor importance. However, the hollow cylinders should advantageously have a size which allows unhindered diffusion of the reaction gases at a very large part of the catalytically active external and internal surface coated with silver particles and optionally with further promoters of the alumina supports.

In particular, the hollow cylinders have a length in the range from 5 to 10 mm, an external diameter in the range from 5 to 10 mm and a ratio of external diameter in mm to wall thickness in mm in the range from 2.5 to 4.5. For example, the following geometries of hollow cylinders (external diameter× length×internal diameter, in each case reported in mm) which are particularly preferred for the purposes of the invention are comprised: 5×5×2, 6×6×3, 7×7×3, 8×8×3, 8×8.5×3, 8×8.5× 3.5, 8.5×8×3.5, 8.5×8×3, 9×9×3, 9.5×9×3, 9.5×9×3.5, where each of these lengths indicated comprises tolerances in the range±0.5 mm.

The present invention accordingly provides a shaped catalyst body as described above and a process for producing a shaped catalyst body as described above and also a shaped catalyst body which has been or can be produced by this process as described above, wherein the shaped catalyst body has the geometry of a hollow cylinder and the hollow cylinder has a length L in the range from 5 to 10 mm, an external diameter $d_A$ in the range from 5 to 10 mm and a ratio of external diameter $d_A$ in mm to the wall thickness $d_W$ in mm in the range from 2.5 to 4.5.

The hollow cylinder preferably has a length in the range from 6 mm to 9.5 mm, more preferably in the range from 6 mm to 9 mm and particularly preferably a length in the range from 6 mm to 8.5 mm.

The hollow cylinder preferably has an external diameter in the range from 6 mm to 9.5 mm, more preferably in the range from 6 mm to 9 mm and particularly preferably an external diameter in the range from 6 mm to 8.5 mm.

The hollow cylinder preferably has a length in the range from 6 mm to 9.5 mm and an external diameter in the range from 6 mm to 9.5 mm, more preferably a length in the range from 6 mm to 9 mm and an external diameter in the range from 6 mm to 9 mm and particularly preferably a length in the range from 6 mm to 8.5 mm and an external diameter in the range from 6 mm to 9 mm.

The ratio of external diameter $d_A$ in mm to the wall thickness $d_W$ in mm is preferably in the range from 3.0 to 4.0.

Amount of Rhenium

As regards the amount of rhenium $C_R$, the catalyst preferably comprises rhenium in an amount of from 210 ppm by weight to 540 ppm by weight, more preferably in an amount of from 250 ppm by weight to 510 ppm by weight, more preferably in an amount of from 280 ppm by weight to 480 ppm by weight and particularly preferably in an amount of from 300 ppm by weight to 450 ppm by weight, based on the total weight of the catalyst and calculated as element, where $C_R$/ppm by weight, based on the wall thickness of the hollow cylinder $d_W$ in mm, is in the range $120 \leq C_R/d_W \leq 200$.

$C_R$/ppm by weight, based on the wall thickness of the hollow cylinder $d_W$ in mm, is preferably in the range $115 \leq C_R/d_W \leq 200$, more preferably in the range $130 \leq C_R/d_W \leq 195$ and particularly preferably in the range $140 \leq C_R/d_W \leq 195$.

Support

The term "alumina" as used here comprises all conceivable structures such as alpha-, gamma- or theta-alumina. In a preferred embodiment, the alumina support is an alpha-alumina support.

In a further preferred embodiment, the alpha-alumina has a purity of at least 75%, preferably a purity of at least 80%, more preferably a purity of at least 85%, more preferably a purity of at least 90%. For example, the alpha-alumina has a purity of at least 98%, of at least 98.5% or of at least 99%.

The term alpha-alumina therefore also comprises alpha-aluminas which comprise further constituents, in particular constituents selected from the group consisting of zirconium, alkali metals, alkaline earth metals, silicon, zinc, gallium, hafnium, boron, fluorine, copper, nickel, manganese, iron, cerium, titanium, chromium and mixtures of two or more thereof.

The alpha-alumina can comprise the constituents in any suitable form, for example as element or in the form of one or more compounds. If the alpha-alumina comprises one or more constituents in the form of a compound, it comprises the latter as, for example, oxide or mixed oxide.

As regards the amount of the further constituents, the total content of the further constituents is preferably in the range of less than 25% by weight, more preferably less than 20% by weight, more preferably less than 15% by weight and more preferably less than 10% by weight, based on the total weight of the alumina support and calculated as the sum of the elements other than aluminum and oxygen.

If the alumina support comprises, for example, silicon, it preferably comprises this in an amount in the range of up to 10000 ppm by weight, preferably in the range from 10 ppm by weight to 8000 ppm, more preferably in an amount of from 50 ppm by weight to 5000 ppm by weight, more preferably in an amount of from 200 ppm by weight to 2800 ppm by weight, based on the total weight of the alumina support and calculated as element. In a particularly preferred embodiment of the invention, the alumina support is an alpha-alumina support, where the alpha-alumina has a purity of at least 85% and comprises silicon in an amount of up to 10 000 ppm by weight, preferably in the range from 10 ppm by weight to 8000 ppm by weight, more preferably in an amount of from 50 ppm by weight to 5000 ppm by weight, more preferably in an amount of from 200 ppm by weight to 2800 ppm by weight, based on the total weight of the alumina support and calculated as element.

If the alumina support comprises, for example, alkali metals, it preferably comprises these in a total amount in the range of not more than 2500 ppm by weight, more preferably in a total amount of from 10 ppm by weight to 1500 ppm by weight, more preferably in a total amount of from 50 ppm by weight to 1000 ppm by weight, based on the total weight of the alumina support and calculated as element.

In a preferred embodiment, the alumina support comprises at least one alkali metal, in particular sodium and/or potassium.

The present invention therefore also provides a shaped catalyst body as described above and a process for producing a shaped catalyst body as described above and also a shaped catalyst body which is obtainable or obtained by this process, where the alumina support comprises at least one alkali metal, in particular sodium and/or potassium.

If the alumina support comprises sodium, it preferably comprises this in an amount in the range from 10 ppm by weight to 1500 ppm by weight, more preferably in an amount of from 10 ppm by weight to 800 ppm by weight, more preferably in an amount of from 10 ppm by weight to 7000 ppm by weight, more preferably in an amount of from 10 ppm by weight to 500 ppm by weight, based on the total weight of the alumina support and calculated as element, where the total amount of all alkali metals as described above is preferably in the range from 10 ppm by weight to 2500 ppm by weight.

If the alumina support comprises potassium, it preferably comprises this in an amount of not more than 1000 ppm by weight, more preferably in an amount of not more than 500 ppm by weight, more preferably in an amount of not more than 200 ppm by weight, for example in the range from 10 ppm by weight to 100 ppm by weight, based on the total weight of the alumina support and calculated as element, where the total amount of all alkali metals as described above is preferably in the range from 10 ppm by weight to 2500 ppm by weight.

In a preferred embodiment of the invention, the alumina support comprises sodium in an amount of from 10 ppm by weight to 1500 ppm by weight and potassium in an amount of not more than 1000 ppm by weight.

In a further embodiment, the alumina support comprises at least one alkaline earth metal. If the alumina support comprises at least one alkaline earth metal, it preferably additionally comprises at least one alkali metal as described above.

If the alumina support comprises at least one alkaline earth metal, it preferably comprises a total amount of alkaline earth metals in the range of not more than 2500 ppm by weight, for example in the range from 1 to 2500 ppm by weight, more preferably in an amount of from 10 to 1200 ppm by weight, more preferably in an amount of from 100 to 800 ppm by weight, based on the total weight of the alumina support and calculated as element. The expression "total amount of alkaline earth metals" as used here relates to the sum of all alkaline earth metals which may be comprised in the alumina support, based on the total weight of the alumina support and in each case calculated as element.

In one embodiment of the invention, the alumina support comprises at least one alkaline earth metal selected from the group consisting of calcium and magnesium. If the alumina support comprises, for example, calcium, it preferably comprises this in an amount in the range from 10 ppm by weight to 1500 ppm by weight, more preferably in an amount of from 20 ppm by weight to 1000 ppm by weight, more preferably in an amount of from 30 ppm by weight to 700 ppm by weight, based on the total weight of the alumina support and calculated as element.

If the alumina support comprises, for example, magnesium, it preferably comprises this in an amount in the range of not more than 800 ppm by weight, preferably in an amount of from 1 ppm by weight to 500 ppm by weight, more preferably in an amount of from 1 ppm by weight to 250 ppm by weight, more preferably in an amount of from 1 ppm by weight to 100 ppm by weight, based on the total weight of the alumina support and calculated as element.

The present invention accordingly provides a shaped catalyst body as described above and a process for producing a shaped catalyst body as described above and also a shaped catalyst body which is obtainable or obtained by this process, where the alumina support comprises magnesium in an amount of not more than 800 ppm by weight and calcium in an amount of from 10 ppm by weight to 1500 ppm by weight, in each case based on the total weight of the alumina support and calculated as element.

The alumina support particularly preferably comprises sodium in an amount of from 10 ppm by weight to 1500 ppm by weight, potassium in an amount of not more than 1000 ppm by weight, magnesium in an amount of not more than 800 ppm by weight and calcium in an amount of from 10 ppm by weight to 1500 ppm by weight, in each case based on the total weight of the alumina support and calculated as element.

For the purposes of the invention, particular preference is given to the alumina support comprising zirconium. If the alumina support comprises zirconium, it preferably comprises this in an amount in the range from 1 ppm by weight to 10000 ppm by weight, more preferably in the range from 10 ppm by weight to 8000 ppm by weight, more preferably in the range from 50 ppm by weight to 6000 ppm by weight and particularly preferably in the range from 50 ppm by weight to 5000 ppm by weight, calculated as metal and based on the total weight of the alumina support.

The alumina support according to the present invention can further comprise zinc as constituent. If the alumina support comprises zinc as constituent, it comprises this in an amount of not more than 800 ppm by weight, preferably in an amount of not more than 600 ppm by weight, more preferably in an amount in the range from 1 ppm by weight to 400 ppm by weight, calculated as element and based on the total weight of the alumina support.

If the alumina support comprises further constituents, for example constituents selected from the group consisting of gallium, hafnium, boron, fluorine, copper, nickel, manganese, iron, cerium, titanium and chromium, it preferably comprises each of these in an amount of not more than 500 ppm by weight, in each case calculated as metal and based on the total weight of the alumina support.

The alumina supports used according to the invention preferably have a BET surface area determined in accordance with DIN ISO 9277 of from 0.1 to 5 m²/g, more preferably in the range from 0.1 to 2 m²/g, more preferably in the range from 0.5 to 1.5 m²/g, more preferably in the range from 0.63 to 1.3 m²/g, more preferably in the range from 0.65 to 1.2 m²/g and particularly preferably in the range from 0.7 to 1.2 m²/g such as in the range from 0.7 to 1.1 m²/g.

The present invention accordingly provides a shaped catalyst body as described above and a process for producing a shaped catalyst body as described above and also a shaped catalyst body which has been or can be produced by this process, wherein the alumina support has a BET surface area determined in accordance with DIN ISO 9277 in the range from 0.1 to 5 m²/g, more preferably in the range from 0.1 to 2 m²/g, more preferably in the range from 0.5 to 1.5 m²/g, more preferably in the range from 0.63 to 1.3 m²/g, more preferably in the range from 0.65 to 1.2 m²/g and particularly preferably in the range from 0.7 to 1.2 m²/g.

Furthermore, the alumina supports according to the invention preferably have pores having diameters in the range from 0.1 to 100 µm, where the pore distribution can be monomodal or polymodal, for example bimodal. The alumina supports preferably have a bimodal pore distribution.

The present invention therefore also provides a shaped catalyst body as described above and a process for producing a shaped catalyst body as described above and also a shaped catalyst body which is obtainable or obtained by this process, wherein the alumina support, preferably the alpha-alumina support, has a bimodal pore distribution.

The alumina supports more preferably have a bimodal pore distribution having peak maxima in the range from 0.1 µm to 10 µm and from 15 µm to 100 µm, preferably in the range from 0.1 µm to 5 µm and from 17 µm to 90 µm, more preferably in the range from 0.1 µm to 3 µm and from 20 µm to 80 µm, more preferably in the range from 0.1 µm to 2.0 µm and from 20 µm to 70 µm. The pore diameters are determined by Hg porosimetry (DIN 66133).

The present invention therefore also provides a shaped catalyst body as described above and a process for producing a shaped catalyst body as described above and also a shaped catalyst body which is obtainable or obtained by this process, where the alumina support has a bimodal pore distribution, preferably a bimodal pore distribution comprising at least pores having pore diameters in the range from 0.1 µm to 10 µm and pores having pore diameters in the range from 15 µm to 100 µm, determined by Hg porosimetry in accordance with DIN 66133. The water absorption of the alumina supports is preferably in the range from 0.35 ml/g to 0.65 ml/g, preferably in the range from 0.42 ml/g to 0.52 ml/g, determined by vacuum cold water uptake.

In general, such alumina supports are produced by mixing the alumina support material, in particular the alumina, with addition of at least one binder or at least one extrusion aid or at least one pore former or at least one water-comprising composition or a mixture of two or more thereof and subsequently shaping the mixture to give a shaped body.

Suitable pore formers are, for example, cellulose and cellulose derivatives, e.g. carboxymethylcellulose, polyolefins such as polyethylenes and polypropylenes. The pore formers are usually removed essentially completely, preferably completely, by means of subsequent calcination of the alumina support.

Suitable binders are, for example, alumina gels with nitric acid or acetic acid, cellulose, methylcellulose, ethylcellulose, carboxyethylcellulose, methyl or ethyl stearate, waxes, polyolefin oxides. Suitable extrusion aids are, for example, described in EP 0496 386 B2, page 3 [0019-0021].

The shaped body obtained as described above is usually optionally dried after shaping and calcined to give the alumina support as per (a). Calcination is usually carried out at temperatures in the range from 1200° C. to 1600° C. The alumina support is often additionally washed after calcination in order to remove soluble constituents.

Alumina supports are, for example, commercially available from N or Pro Co.

Silver

Apart from rhenium, the shaped catalyst body as described above comprises silver as active metal applied to the alumina support. As regards the amount of silver, the shaped catalyst body preferably comprises silver in an amount of from 5 to 30% by weight, more preferably in an amount of from 5 to 25% by weight and particularly preferably in an amount of from 10 to 20% by weight, calculated as element and based on the total weight of the shaped catalyst body.

The present invention accordingly provides a shaped catalyst body as described above comprising silver in an amount of from 5 to 30% by weight, based on the total weight of the shaped catalyst body and calculated as element.

The present invention likewise provides a process for producing a shaped catalyst body as described above and also a shaped catalyst body which is obtainable or obtained by this process, where the process comprises
(a) providing an alumina support which has the geometry of a hollow cylinder,
(b) applying silver and rhenium to the alumina support, with rhenium being applied in an amount of $C_R$/ppm by weight, based on the wall thickness of the hollow cylinder $d_w$ in mm and calculated as element which is in the range $120 \leq C_R/d_w \leq 200$, to the support and silver being applied in an amount of from 5 to 30% by weight, based on the total weight of the shaped catalyst body and calculated as element.

The application of silver to the shaped catalyst body is preferably carried out by bringing the alumina support into contact with at least one mixture G1 comprising at least one silver compound.

As regards the contacting of G1 with the catalyst support, all processes by means of which the mixture can be applied in an appropriate way are generally suitable. The at least one mixture G1 which comprises at least one silver compound is preferably applied by impregnation, spraying or mixing processes to the support. The processes for producing silver catalysts as are disclosed in DE-A 2300512, DE-A 2521906, EP-A 14457, EP-A 85237, EP-A 384312, DE-A 2454972, DE-A 3321895, EP-A 229465, DE-A 3150205, EP-A 172565 and EP-A 357293 may be mentioned by way of example.

The application of silver is particularly preferably effected by vacuum impregnation at room temperature. In the vacuum impregnation, the catalyst support as described above is preferably firstly treated at a pressure in the range of not more than 500 mbar, more preferably at a pressure of not more than 250 mbar and particularly preferably at a pressure of not more than 30 mbar. This is particularly preferably carried out at a temperature in the range from 1° C. to 80° C., more preferably at a temperature in the range from 3° C. to 50° C., more preferably at a temperature in the range from 5° C. to 30° C. and particularly preferably at room temperature. The vacuum treatment is preferably carried out for a time of at least 1 minute, preferably at least 5 minutes, more preferably for a time in the range from 5 minutes to 120 minutes, in particular in the range from 10 minutes to 45 minutes, particularly preferably in the range from 10 minutes to 30 minutes.

After the vacuum treatment, at least mixture G1 is brought into contact with the catalyst support. Mixture G1 is preferably dripped or sprayed on, preferably sprayed on. Application is preferably carried out by means of a nozzle.

Mixture G1 preferably comprises silver in the form of at least one silver compound. The silver compound is preferably applied as a solution, in particular as a solution in water. G1 therefore preferably further comprises at least one solvent, preferably water. To obtain the silver compound in soluble form, a complexing agent such as at least one amine, in particular ethanolamine, EDTA, 1,3- or 1,2-propanediamine, ethylenediamine, and/or an alkali metal oxalate which can simultaneously also act as reducing agent can be additionally added in a suitable manner to the silver compound, for example silver(I) oxide or silver(I) oxalate. In a preferred embodiment, G1 therefore comprises at least one complexing agent, in particular ethanolamine, EDTA, 1,3- or 1,2-propanediamine, ethylene-diamine and/or an alkali metal oxalate.

If G1 comprises at least one complexing agent, G1 comprises at least part of the silver in the form of a silver complex. G1 particularly preferably comprises at least part of the silver as a cationic silver-oxalato-ethylenediamine compound. G1 particularly preferably comprises water, silver-oxalato-ethylenediamine complexes and optionally excess ethylenediamine.

As regards the concentration of the silver-comprising compound in G1, this is preferably in the range from 25 to 35%, more preferably in the range from 26 to 32% and more preferably in the range from 27 to 30%.

As indicated above, silver is applied to the alumina support in an amount, calculated as elemental Ag, of from 5 to 30% by weight, more preferably in an amount of from 5 to 25% by weight and particularly preferably in an amount of from 10 to 20% by weight, calculated as element and based on the total weight of the shaped catalyst body, in step (b).

The application in (b) can be carried out in more than one step, for example in 2, 3 or 4 steps. The alumina support can optionally be dried and/or calcined between each of the individual steps. If the application according to (b) is carried out in more than one step, the total amount of silver applied to the alumina support after all steps is likewise in the range from 5 to 30% by weight, more preferably in the range from 5 to 25% by weight and particularly preferably in an amount of from 10 to 20% by weight, calculated as element and based on the total weight of the shaped catalyst body as described above.

The application of the silver can be followed by at least one after-treatment step, for example a drying step, e.g. one, two or more drying steps. Drying is usually carried out at temperatures in the range from 2 to 200° C. The after-treatment step is preferably drying by means of vacuum treatment as described above. This evacuation is preferably carried out at a pressure in the range of not more than 500 mbar, more preferably at a pressure of not more than 250 mbar and particularly preferably at a pressure of not more than 30 mbar. The vacuum treatment is preferably carried out at a temperature in the range from 2 to 50° C., more preferably at a temperature in the range from 5 to 30° C. and particularly preferably at room temperature. The vacuum treatment is carried out for a time of at least 1 minute, preferably at least 5 minutes, more preferably for a time in the range from 5 minutes to 120 minutes, in particular in the range from 10 minutes to 45 minutes, particularly preferably in the range from 10 minutes to 20 minutes.

The application of the silver and optionally the at least one drying step is/are preferably followed by at least one calcination step.

Rhenium

The shaped catalyst body of the invention comprises at least rhenium as promoter in addition to silver.

Rhenium is preferably applied to the support by impregnation or spraying or mixing processes as described above for silver.

As regards the point in time at which rhenium is applied, this can be after the application of silver and/or after any of the at least one after-treatment step has been carried out. As an alternative, it is possible to apply the rhenium together with the silver compound or before application of the silver compound to the support. If the rhenium is applied to the alumina support before the silver, at least one after-treatment step, for example a drying step, e.g. one, two or more drying steps, and/or, for example, at least one calcination step can be carried out before the application of silver. Particular preference is given to applying rhenium simultaneously with silver to the alumina support in step (b). Here, the rhenium can be applied to the support in parallel to the application of silver, preferably in the form of at least one rhenium compound, in a mixture G2. G1 preferably also comprises rhenium and/or at least one rhenium compound in addition to the at least one silver compound.

The rhenium is particularly preferably applied as a compound, for example as a halide, oxyhalide, oxide or as acid. Furthermore, rhenium can be used in the form of salts of heteropolyacids of rhenium, for example as rhenate or perrhenate, in the production process of the invention.

The present invention therefore also provides a process as described above and a catalyst which is obtainable or obtained by this process comprising
(a) providing an alumina support which has the geometry of a hollow cylinder,
(b) applying silver and rhenium to the alumina support by bringing the alumina support into contact with at least one mixture G1 comprising at least one silver compound and at least one rhenium compound, with contacting preferably being carried out by means of vacuum impregnation and with rhenium being applied in an amount of $C_R$/ppm by weight, based on the wall thickness of the hollow cylinder $d_W$ in mm and calculated as element which is in the range $120 \leq C_R/d_W \leq 200$, to the support and silver being applied in an amount of from 5 to 30% by weight, based on the total weight of the shaped catalyst body and calculated as element.

In step b), rhenium is preferably applied as a compound to the alumina support, with the compound being selected from the group consisting of ammonium perrhenate, rhenium(III) chloride, rhenium(V) chloride, rhenium(V) fluoride, rhenium (VI) oxide and rhenium(VII) oxide. For the purposes of the invention, rhenium is particularly preferably applied as ammonium perrhenate to the alumina support.

Further Promoters

Apart from rhenium, the shaped catalyst body can comprise at least one further promoter. The shaped catalyst body particularly preferably comprises at least one further promoter.

The invention therefore comprises, for example, embodiments in which the shaped catalyst body comprises five different promoters, four different promoters, three different promoters, two different promoters or one further promoter applied in addition to rhenium to the alumina support. In particular, this at least one further promoter is selected from among elements of groups IA, VIIB, VIIB and VIA of the Periodic Table of the Elements, particularly preferably selected from the group consisting of tungsten, lithium, sulfur, cesium, chromium, manganese, molybdenum and potassium.

The present invention accordingly provides a shaped catalyst body as described above and a process for producing a shaped catalyst body as described above and also a shaped catalyst body which is obtainable or obtained by this process, wherein the shaped catalyst body comprises at least one further promoter selected from the group consisting of elements of groups IA, VIIB, VIIB and VIA, preferably selected from the group consisting of tungsten, cesium, lithium and sulfur.

In a particularly preferred embodiment, the catalyst comprises at least cesium, lithium, tungsten and sulfur as promoters in addition to rhenium.

If the shaped catalyst body comprises at least one further promoter, it preferably comprises a total amount of these further promoters in an amount of from 10 ppm by weight to 2000 ppm by weight, preferably in an amount of from 10 to 1700 ppm, more preferably in each case in an amount of from 50 ppm by weight to 1500 ppm by weight and particularly preferably in each case in an amount of from 80 ppm by weight to 1200 ppm by weight, based on the total weight of the shaped catalyst body and calculated as sum of the elements.

If the shaped catalyst body comprises tungsten as promoter, as described above, the tungsten is preferably applied as tungsten compound to the support. Here, it is in principle possible to use any suitable tungsten compound. Preference is given to applying tungsten in the form of tungstate or tungstic acid. The shaped catalyst body preferably comprises tungsten as promoter in an amount of up to 800 ppm by weight, preferably in an amount in the range from 5 to 500 ppm by weight, more preferably in an amount in the range from 100 to 300 ppm by weight, based on the total weight of the shaped catalyst body and calculated as element.

If the shaped catalyst body comprises lithium as promoter as described above, the lithium is preferably applied as lithium compound to the support. Here, it is in principle possible to use any suitable lithium compound. Lithium is preferably applied in the form of lithium nitrate. If the shaped catalyst body comprises lithium as promoter, it preferably comprises lithium in an amount of up to 700 ppm by weight, preferably in an amount in the range from up to 10 ppm by weight to 500 ppm by weight, more preferably in an amount in the range from 80 ppm by weight to 250 ppm by weight, based on the total weight of the shaped catalyst body and calculated as element.

If the shaped catalyst body comprises cesium as promoter as described above, the cesium is preferably applied as cesium compound to the support. Here, it is in principle possible to use any suitable cesium compound. Cesium is preferably applied in the form of cesium hydroxide. If the shaped catalyst body comprises cesium as promoter, it preferably comprises cesium in an amount of up to 1500 ppm by weight, preferably in an amount in the range from up to 100 ppm by weight to 800 ppm by weight, more preferably in an amount in the range from 200 ppm by weight to 600 ppm by weight, based on the total weight of the shaped catalyst body and calculated as element.

If the shaped catalyst body comprises sulfur as promoter as described above, the sulfur is preferably applied as a sulfur compound to the support. Here, it is in principle possible to use any suitable sulfur compound. Sulfur is preferably applied in the form of ammonium sulfate. If the shaped catalyst body comprises sulfur as promoter, it preferably comprises sulfur in an amount of from 0 to 50 ppm by weight, more preferably in an amount in the range from 1 ppm by weight to 25 ppm by weight, based on the total weight of the shaped catalyst body and calculated as element.

The present invention accordingly provides a shaped catalyst body as described above and a process for producing a shaped catalyst body as described above and also a shaped catalyst body which is obtainable or obtained by this process, wherein the shaped catalyst body comprises tungsten in an amount in the range from 5 ppm by weight to 500 ppm by weight, cesium in an amount in the range from 100 ppm by weight to 800 ppm by weight, lithium in an amount in the range from 10 ppm by weight to 500 ppm by weight and sulfur in an amount in the range from 0 to 50 ppm by weight, based on the total weight of the shaped catalyst body and calculated as element.

If the shaped catalyst body comprises at least one further promoter, this at least one further promoter is preferably applied in the form of compounds, for example in the form of complexes or in the form of salts, for example in the form of halides, for example in the form of fluorides, bromides or chlorides, or in the form of carboxylates, nitrates, sulfates or sulfides, phosphates, cyanides, hydroxides, carbonates or as salts of heteropolyacids, to the support in the process of the invention for producing the catalyst.

The at least one further promoter, more preferably the at least one further promoter compound, is preferably dissolved in a suitable solution, preferably in water, before application. The alumina support is then preferably brought into contact (impregnated) with the resulting solution comprising one or more of the further promoters.

If a plurality of further promoters are to be added, these can be applied to the support either together or separately in one step or in a plurality of steps. As regards the solution comprising one or more of the further promoters, this can be produced in any suitable way. For example, the promoters can each be dissolved separately in one solution each and the resulting solutions each comprising one promoter can subsequently be used for impregnation. It is likewise possible for two or more of the further promoters to be dissolved together in one solution and the resultant solution to be used subsequently for the impregnation. In addition, it is possible for the resulting solutions comprising at least one promoter to be combined before impregnation and the resulting solution comprising all promoters to be applied to the support.

As regards the point in time at which the at least one further promoter is applied, the application can be carried out after the application of silver and/or rhenium and/or after at least one optional after-treatment step has been carried out. As an alternative, it is possible to apply the at least one further promoter together with the silver compound and/or the rhenium compound or before the silver compound and/or the rhenium compound to the support.

Particular preference is given to applying the at least one further promoter simultaneously with silver and rhenium to the alumina support in step (b). Here, the at least one further promoter can be applied in parallel to the application of silver and rhenium, in a separate mixture G3 to the support.

The at least one further promoter is preferably applied as constituent of the mixture G1, which preferably comprises rhenium and/or at least one rhenium compound in addition to the at least one silver compound, to the alumina support. The at least one further promoter is accordingly preferably applied together with rhenium and silver to the alumina support.

Particular preference is given to all further promoters comprised in the shaped catalyst body being applied together with rhenium and silver to the alumina support.

The present invention therefore also provides a process as described above and a catalyst which is obtainable or obtained by this process, which comprises
(a) providing an alumina support which has the geometry of a hollow cylinder,
(b) applying silver, rhenium and at least one further promoter to the alumina support by bringing the alumina support into contact with at least one mixture G1 comprising at least one silver compound and at least one rhenium compound and at least one further promoter in the form of at least one compound, with contacting preferably being carried out by means of vacuum impregnation and with rhenium being applied in an amount of $C_R$/ppm by weight, based on the wall thickness of the hollow cylinder $d_W$ in mm and calculated as element which is in the range $120 \leq C_R/d_w \leq 200$, to the support and silver being applied in an amount of from 5 to 30% by weight, based on the total weight of the shaped catalyst body and calculated as element.

If, for example, at least cesium, tungsten, lithium, sulfur are used as further promoters, a particularly preferred embodiment comprises producing at least one solution comprising cesium (in the form of at least one compound) and tungsten (in the form of at least one compound), a further solution comprising lithium (in the form of at least one compound) and sulfur (in the form of at least one compound) and a further solution comprising rhenium (in the form of at least one compound).

In one embodiment, the solutions are applied to the support in separate impregnation steps. Particular preference is given to combining the solutions with a solution comprising at least one silver compound to give the mixture G1. Thus, G1 particularly preferably comprises in addition to the at least one silver compound, at least one rhenium compound, at least one cesium compound, at least one lithium compound, at least one tungsten compound and optionally further promoters, in each case in the form of at least one compound.

The present invention accordingly provides a shaped catalyst body as described above and a process for producing a shaped catalyst body as described above and also a shaped catalyst body which is obtainable or obtained by this process, where the catalyst additionally comprises at least one further promoter selected from among elements of groups IA, VIIB, VIIB and VIA of the Periodic Table of the Elements, preferably selected from the group consisting of tungsten, lithium, sulfur, cesium, chromium, manganese, molybdenum and potassium, and the at least one further promoter is preferably applied to the alumina support by bringing the alumina support into contact, preferably by means of vacuum impregnation, with the mixture G1 which additionally comprises the at least one promoter, in step (b).

In a particularly preferred embodiment, the catalyst comprises tungsten in an amount of from 100 ppm by weight to 500 ppm by weight, cesium in an amount of from 100 ppm by weight to 800 ppm by weight, lithium in an amount of from 10 ppm by weight to 500 ppm by weight and sulfur in an amount of from 0 to 50 ppm by weight.

The present invention accordingly provides a shaped catalyst body as described above and a process for producing a shaped catalyst body as described above and also a shaped catalyst body which is obtainable or obtained by this process, where the shaped catalyst body comprises tungsten in an amount of from 100 ppm by weight to 500 ppm by weight, cesium in an amount of from 100 ppm by weight to 800 ppm, lithium in an amount of from 10 ppm by weight to 500 ppm by weight and sulfur in an amount of from 0 to 50 ppm by weight.

Step (c)

Step (b) can be followed by at least one after-treatment step, for example a drying step, e.g. one, two or more drying steps. Drying is usually carried out at temperatures in the range from 2 to 200° C. For example, the after-treatment step is drying by means of vacuum treatment as described above. This evacuation is preferably carried out at a pressure in the range of not more than 500 mbar, more preferably at a pressure of not more than 250 mbar and particularly preferably at a pressure of not more than 30 mbar. The vacuum treatment is preferably carried out at a temperature in the range from 2° C. to 50° C., more preferably at a temperature in the range from 5° C. to 30° C. and particularly preferably at room temperature. The vacuum treatment is carried out for a time of at least 1 minute, preferably at least 5 minutes, more preferably for a time in the range from 5 minutes to 120 minutes, in particular in the range from 10 minutes to 45 minutes, particularly preferably in the range from 10 minutes to 20 minutes.

The optionally dried alumina support according to (b) is preferably calcined. The present invention therefore also provides a process as described above and a catalyst which is obtainable or obtained by this process, which comprises
(c) drying and/or calcining the alumina support according to (b) to give the shaped catalyst body.

If a calcination is carried out in step (c), this calcination is preferably carried out at temperatures in the range from 150 to 750° C., preferably in the range from 200 to 500° C. and particularly preferably in the range from 220 to 350° C., with the calcination time generally being at least 5 minutes or more, for example in the range from 5 minutes to 24 hours or in the range from 10 minutes to 12 hours.

The calcination time is particularly preferably in the range from 5 minutes to 3 hours. The calcination can be carried out at a constant temperature, but embodiments in which the temperature is changed continuously or discontinuously during the calcination time are also comprised.

The calcination can be carried out under any gas atmosphere suitable for this purpose, for example in an inert gas or a mixture of an inert gas and from 10 ppm to 21% by volume of oxygen. As inert gas, mention may be made by way of example of nitrogen, argon, carbon dioxide, helium and combinations of at least two of the abovementioned inert gases. If the calcination is carried out in an inert gas, particular preference is given to nitrogen. In an alternative preferred embodiment, air and/or lean air is used.

Furthermore, the calcination is preferably carried out in a muffle furnace, convection oven, in a rotary furnace and/or a belt calcination furnace.

Process for Preparing Ethylene Oxide

The shaped catalyst bodies of the invention or the shaped catalyst bodies which are obtainable or obtained by a process according to the invention are particularly suitable as catalysts for preparing ethylene oxide from ethylene in a process comprising oxidation of ethylene. High selectivities, in particular advantageous initial selectivities, and good activities are achieved.

The present invention therefore also provides, according to a further aspect, a process for preparing ethylene oxide from ethylene, which comprises oxidation of ethylene in the presence of a shaped catalyst body for the preparation of ethylene oxide as described above.

In addition, the present invention also provides for the use of a shaped catalyst body as described above for preparing ethylene oxide by gas-phase oxidation of ethylene.

According to the invention, the epoxidation can be carried out by all processes known to those skilled in the art. It is possible to use all reactors which can be used in the ethylene oxide production processes of the prior art; for example externally cooled shell-and-tube reactors (cf. Ullmann's Encyclopedia of Industrial Chemistry, 5th edition, vol. A-10, pp. 117-135, 123-125, VCH-Verlagsgesellschaft, Weinheim 1987) or reactors having a loose catalyst bed and cooling tubes, for example the reactors described in DE-A 3414717, EP 0082609 and EP-A 0339748. The epoxidation is preferably carried out in at least one tube reactor, preferably in a shell-and-tube reactor. To prepare ethylene oxide from ethylene and oxygen, it is possible according to the invention to carry out the reaction under conventional reaction conditions as described, for example, in DE-A 2521906, EP-A 0 014 457, DE-A 2300512, EP-A 0 172 565, DE-A 2454972, EP-A 0 357 293, EP-A 0 266 015, EP-A 0 085 237, EP-A 0 082 609 and EP-A 0 339 748. Inert gases such as nitrogen or gases which are inert under the reaction conditions, e.g. steam, methane, and also optionally reaction moderators, for example halogenated hydrocarbons such as ethyl chloride, vinyl chloride or 1,2-dichloroethane can additionally be mixed into the reaction gas comprising ethylene and molecular oxygen. The oxygen content of the reaction gas is advantageously in a range in which no explosive gas mixtures are present. A suitable composition of the reaction gas for preparing ethylene oxide can, for example, comprise an amount of ethylene in the range from 10 to 80% by volume, preferably from 20 to 60% by volume, more preferably from 25 to 50% by volume and particularly preferably in the range from 30 to 40% by volume, based on the total volume of the reaction gas. The oxygen content of the reaction gas is advantageously in the range of not more than 10% by volume, preferably not more than 9% by volume, more preferably not more than 8% by volume and very particularly preferably not more than 7% by volume, based on the total volume of the reaction gas.

The reaction gas preferably comprises a chlorine-comprising reaction moderator such as ethyl chloride, vinyl chloride or dichloroethane in an amount of from 0 to 15 ppm by weight, preferably in an amount of from 0.1 to 8 ppm by weight. The remainder of the reaction gas generally comprises hydrocarbons such as methane and also inert gases such as nitrogen. In addition, other materials such as steam, carbon dioxide or noble gases can also be comprised in the reaction gas.

The above-described constituents of the reaction mixture may optionally each have small amounts of impurities. Ethylene can, for example, be used in any degree of purity suitable for the gas-phase oxidation according to the invention. Suitable degrees of purity include, but are not limited to, "polymer-grade" ethylene which typically has a purity of at least 99% and "chemical-grade" ethylene which typically has a purity of less than 95%. The impurities typically comprise, in particular, ethane, propane and/or propene.

The reaction or oxidation of ethylene to ethylene oxide is usually carried out at elevated temperature. Preference is given to temperatures in the range from 150 to 350° C., more preferably in the range from 180 to 300° C., more preferably temperatures in the range from 190° C. to 280° C. and particularly preferably temperatures in the range from 200° C. to 280° C. The present invention therefore also provides a process as described above in which the oxidation is carried out at a temperature in the range 180-300° C., preferably in the range from 200 to 280° C.

The reaction according to the invention (oxidation) is preferably carried out at pressures in the range from 5 bar to 30 bar. The oxidation is more preferably carried out at a pressure in the range from 5 bar to 25 bar, preferably at a pressure in the range from 10 bar to 20 bar and in particular in the range from 14 bar to 20 bar. The present invention therefore also provides a process as described above in which the oxidation is carried out at a pressure in the range from 14 bar to 20 bar.

The oxidation is preferably carried out in a continuous process. If the reaction is carried out continuously, the GHSV (gas hourly space velocity) is, depending on the type of reactor chosen, for example on the size/cross-sectional area of the reactor, the shape and size of the catalyst, preferably in the range from 800 to 10 000/h, preferably in the range from 2000 to 6000/h, more preferably in the range from 2500 to 5000/h, where the values indicated are based on the volume of the catalyst.

The preparation of ethylene oxide from ethylene and oxygen can advantageously be carried out in a recycle process. Here, the reaction mixture is circulated through the reactor with the newly formed ethylene oxide and also the by-products formed in the reaction being removed from the product gas stream after each pass and the product gas stream being, after having been supplemented with the required amounts of ethylene, oxygen and reaction moderators, reintroduced into the reactor. The separation of the ethylene oxide from the product gas stream and its work-up can be carried out by customary methods of the prior art (cf. Ullmann's Encyclopedia of Industrial Chemistry, 5th edition, vol. A-10, pp. 117-135, 123-125, VCH-Verlagsgesellschaft, Weinheim 1987).

Particularly preferred embodiments of the invention are indicated below:

1. A shaped catalyst body for preparing ethylene oxide, which comprises at least silver and rhenium applied to an alumina support, wherein the alumina support has the geometry of a hollow cylinder, and the shaped catalyst body has a rhenium content $C_R$ and $C_R$/ppm by weight, based on the wall thickness of the hollow cylinder $d_W$ in mm, in the range $120 \leq C_R/d_W \leq 200$.
2. The shaped catalyst body according to embodiment 2, wherein the hollow cylinder has a length L in the range from 5 to 10 mm, an external diameter $d_A$ in the range from 5 to 10 mm and a ratio of external diameter $d_A$ in mm to the wall thickness $d_W$ in mm in the range from 2.5 to 4.5.
3. The shaped catalyst body according to embodiment 2, wherein the hollow cylinder has a length L in the range from 6 to 9.5 mm.
4. The shaped catalyst body according to any of embodiments 1 to 3, wherein the shaped catalyst body comprises silver in an amount of from 5 to 30% by weight, based on the total weight of the shaped catalyst body and calculated as element.
5. The shaped catalyst body according to any of embodiments 1 to 4, wherein the alumina support, preferably the alpha-alumina support, has a bimodal pore distribution.
6. The shaped catalyst body according to any of embodiments 1 to 5, wherein the alumina support has a BET surface area in the range from 0.7 to 1.2 m²/g.
7. The shaped catalyst body according to any of embodiments 1 to 6, wherein the alumina support comprises calcium in an amount in the range from 10 ppm by weight to 1500 ppm by weight, based on the total weight of the support and calculated as element.
8. The shaped catalyst body according to any of embodiments 1 to 7, wherein the alumina support comprises magnesium in an amount in the range of not more than 800 ppm by weight, preferably in an amount of from 1 ppm by weight to 500 ppm by weight, based on the total weight of the support and calculated as element.
9. The shaped catalyst body according to any of embodiments 1 to 8, wherein the alumina support comprises potassium in an amount in the range of not more than 1000 ppm by weight, based on the total weight of the support and calculated as element.
10. The shaped catalyst body according to any of embodiments 1 to 9, wherein the alumina support comprises sodium in an amount in the range from 10 ppm by weight to 1500 ppm by weight, based on the total weight of the support and calculated as element.
11. The shaped catalyst body according to any of embodiments 1 to 10, wherein the alumina support comprises silicon in an amount in the range from 50 ppm by weight to 10000 ppm by weight, more preferably in an amount of from 100 ppm by weight to 5000 ppm by weight, more preferably in an amount of from 1000 ppm by weight to 2800 ppm by weight, based on the total weight of the support and calculated as element.
12. The shaped catalyst body according to any of embodiments 1 to 11, wherein the alumina support comprises zirconium in an amount in the range from 1 ppm by weight to 10 000 ppm by weight, based on the total weight of the support and calculated as element.
13. The shaped catalyst body according to any of embodiments 1 to 12, wherein the catalyst comprises at least one promoter selected from the group consisting of elements of groups IA, VIIB, VIIB and VIA, preferably selected from the group consisting of tungsten, cesium, lithium and sulfur.
14. The shaped catalyst body according to any of embodiments 1 to 13, wherein the shaped catalyst body comprises tungsten in an amount in the range from 5 ppm by weight to 500 ppm by weight, cesium in an amount in the range from 100 ppm by weight to 800 ppm by weight, lithium in an amount in the range from 10 ppm by weight to 500 ppm by weight and sulfur in an amount in the range from 0 to 50 ppm by weight, calculated as element and based on the total weight of the shaped catalyst body.
15. A process for producing a shaped catalyst body comprising silver and rhenium applied to an alumina support, which comprises
    (a) providing an alumina support which has the geometry of a hollow cylinder,
    (b) applying silver and rhenium to the alumina support, with rhenium being applied in an amount of $C_R$/ppm by weight, based on the wall thickness of the hollow cylinder $d_W$ in mm and calculated as element which is in the range $120 \leq C_R/d_w \leq 200$, to the alumina support.
16. The process according to embodiment 15, wherein the process further comprises
    (c) calcining the alumina support obtained according to (b).
17. The process according to embodiment 15 or 16, wherein silver is applied in an amount of from 5 to 30% by weight, based on the total weight of the shaped catalyst body and calculated as element, in (b).
18. A shaped catalyst body which is obtainable or obtained by a process according to any of embodiments 15 to 17.
19. A process for preparing ethylene oxide by gas-phase oxidation of ethylene by means of oxygen in the presence of a shaped catalyst body according to any of embodiments 1 to 14 and 18.
20. The use of a shaped catalyst body according to any of embodiments 1 to 14 and 18 as catalyst for preparing ethylene oxide by gas-phase oxidation of ethylene by means of oxygen.

Particularly preferred embodiments of the invention are indicated below, including the embodiments resulting from the combinations given by the back-references being explicitly:

1. A shaped catalyst body for preparing ethylene oxide, which comprises at least silver and rhenium applied to an alumina support, wherein the alumina support has the geometry of a hollow cylinder and the shaped catalyst body has a rhenium content $C_R$, and wherein $C_R$/ppm by weight, based on the wall thickness of the hollow cylinder $d_W$ in mm, is in the range from $120<C_R/d_W<200$.
2. The shaped catalyst body according to embodiment 1, wherein the hollow cylinder has a length L in the range from 5 to 10 mm, an external diameter $d_A$ in the range from 5 to 10 mm and a ratio of external diameter $d_A$ in mm to the wall thickness $d_W$ in mm in the range from 2.5 to 4.5.
3. The shaped catalyst body according to embodiment 2, wherein the hollow cylinder has a length L in the range from 6 to 9.5 mm.
4. The shaped catalyst body according to any of embodiments 1 to 3, wherein the shaped catalyst body comprises silver in an amount of from 5 to 30% by weight, based on the total weight of the shaped catalyst body and calculated as element.
5. The shaped catalyst body according to any of embodiments 1 to 4, wherein the alumina support, preferably the alpha-alumina support, has a bimodal pore distribution.
6. The shaped catalyst body according to any of embodiments 1 to 5, wherein the alumina support has a BET surface area in the range from 0.7 to 1.2 m²/g.
7. The shaped catalyst body according to any of embodiments 1 to 6, wherein the catalyst comprises at least one promoter selected from the group consisting of elements of groups IA, VIIB, VIIB and VIA, preferably selected from the group consisting of tungsten, cesium, lithium and sulfur.
8. The shaped catalyst body according to any of embodiments 1 to 7, wherein the shaped catalyst body comprises tungsten in an amount in the range from 5 ppm by weight to 500 ppm by weight, cesium in an amount in the range from 100 ppm by weight to 800 ppm by weight, lithium in an amount in the range from 10 ppm by weight to 500 ppm by weight and sulfur in an amount in the range from 0 to 50 ppm by weight, calculated as element and based on the total weight of the shaped catalyst body.
9. A process for producing a shaped catalyst body comprising silver and rhenium applied to an alumina support, which comprises
  (a) providing an alumina support which has the geometry of a hollow cylinder,
  (b) applying silver and rhenium to the alumina support, with rhenium being applied in an amount of $C_R$/ppm by weight, based on the wall thickness of the hollow cylinder $d_W$ in mm and calculated as element which is in the range $120<C_R/dw<200$, to the alumina support.
10. The process according to claim 9, wherein the process further comprises
  (c) calcining the alumina support obtained according to (b).
11. The process according to embodiment 9 or 10, wherein silver is applied in an amount of from 5 to 30% by weight, based on the total weight of the shaped catalyst body and calculated as element, in (b).
12. A shaped catalyst body obtainable or obtained by a process according to any of embodiments 9 to 11.
13. A process for preparing ethylene oxide by gas-phase oxidation of ethylene by means of oxygen in the presence of a shaped catalyst body according to any of embodiments 1 to 8 or 12.
14. The use of a shaped catalyst body according to any of embodiments 1 to 8 or 12 as catalyst for preparing ethylene oxide by gas-phase oxidation of ethylene by means of oxygen.

The present invention is illustrated by the following examples.

EXAMPLES

1. General Method for Producing the Catalyst According to the Invention

1.1 Alumina Supports Used

Bimodal alpha-alumina supports having a hollow ring geometry were used. The properties of the alpha-alumina supports are summarized in table 1 below:

TABLE 1

| | Supports used | | | |
|---|---|---|---|---|
| | Support A | Support B | Support C | Support D |
| Ring geometry [mm × mm × mm] | 8.06 × 8.69 × 2.88 | 6.32 × 6.56 × 2.84 | 6.03 × 5.46 × 2.47 | 8.13 × 8.33 × 2.71 |
| BET [m²/g] | 1.12 | 1.00 | 0.75 | 0.72 |
| Water uptake [ml/g] | 0.55 | 0.48 | 0.46 | 0.46 |
| Hg porosimetry Peak maxima [µm] | 1.1, 39.6 | 1.1, 39.6 | 0.94, 61.0 | 1.08, 61.2 |
| Ca [ppm] | 700 | 500 | 600 | 400 |
| Fe [ppm] | — | 100 | <100 | 100 |
| K [ppm] | — | <100 | <100 | 200 |
| Mg [ppm] | — | <100 | 100 | 100 |
| Na [ppm] | 200 | 200 | 300 | 200 |
| Si [ppm] | 2500 | 2400 | 600 | 500 |
| Ti [ppm] | — | <100 | <100 | <100 |
| Zn [ppm] | — | 350 | <100 | <100 |
| Zr [ppm] | 4500 | 4000 | <100 | <100 |

1.2 Preparation of the Silver Complex Solution 1.5 l of water were placed in a vessel and 550 g of silver nitrate were added while stirring and completely dissolved therein. The solution was heated to 40° C. during this procedure. 402.62 g of potassium hydroxide solution (47.8%) were mixed with 1.29 l of water. 216.31 g of oxalic acid were subsequently added and completely dissolved and the solution was heated to 40° C. The potassium oxalate solution was subsequently added to the silver nitrate solution (40° C.) by means of a metering pump over a period of about 45 minutes (volume flow=about 33 ml/min). After the addition was complete, the solution obtained was stirred at 40° C. for a further 1 hour. The precipitated silver oxalate was filtered off and the filter cake obtained was washed with 1 l portions of water (about 10 l) until it was free of potassium and nitrate (determined by means of conductivity measurements on the washings; for the present purposes, free of potassium and nitrate means a conductivity of <40 µS/cm). The water was removed from the filter cake as completely as possible and the residual moisture content of the filter cake was determined. 620 g of silver oxalate having a water content of 20.80% were obtained.

306 g of ethylenediamine were cooled to about 10° C. by means of an ice bath and 245 g of water was added in small portions. After the addition of water was complete, 484.7 g of the (still moist) silver oxalate obtained were added in small portions over a period of about 30 minutes. The mixture was stirred overnight at room temperature and the residue was subsequently centrifuged off. The Ag content of the remaining clear solution was determined by refractometry and the density was determined by means of a 10 ml measuring cylinder.

The solution obtained comprised 29.35% by weight of silver, calculated as element, and had a density of 1.536 g/ml.

1.3 Preparation of the Solution Comprising Silver and Promoters 87.61 g of the silver complex solution were placed in a vessel. 1.11 g of a solution of lithium and sulfur (2.85% by weight of lithium and 0.21% by weight of sulfur), 1.66 g of a solution of tungsten and cesium (2% by weight of tungsten and 3.5% by weight of cesium) and ammonium perrhenate were added thereto and the solution was stirred for 5 minutes.

The amount of ammonium perrhenate is indicated in the respective examples 1 to 12.

1.4 Application of the Solution to the Support 140 g of the respective support as per 1.1 (see table 1) were placed in a rotary evaporator and evacuated at 10 mbar. The support was preevacuated for about 10 minutes.

The solution obtained under 1.4 was dripped onto the support over a period of 15 minutes and the impregnated support was subsequently allowed to rotate under reduced pressure for a further 15 minutes. The support was then left in the apparatus at room temperature and atmospheric pressure for 1 hour and mixed gently every 15 minutes.

1.5 Calcination of the Impregnated Support

The impregnated support was treated at 283° C. under 8.3 m³ of air per hour in a convection oven (HORO, model 129 ALV-SP, catalogue No.: 53270).

1.6 Epoxidation

The epoxidations were carried out in an experimental reactor comprising an upright stainless steel reaction tube having an internal diameter of 6 mm and a length of 2200 mm. The reaction tube provided with a jacket was heated by means of hot oil having the temperature T which flowed through the jacket. To a very good approximation, the temperature of the oil corresponds to the temperature in the reaction tube and thus the reaction temperature. The reaction tube was filled from the bottom upward to a height of 212 mm with inert steatite spheres (1.0-1.6 mm), then to a height of 1100 mm with 38.2 g of crushed catalyst, particle size 0.5-0.9 mm, and then to a height of 707 mm with inert steatite spheres (1.0-1.6 mm). The feed gas entered the reactor from the top and left it again at the lower end after passing through the catalyst bed.

The feed gas comprised 35% by volume of ethylene, 7% by volume of oxygen, 1% by volume of $CO_2$ (EC (ethylene chloride) moderation). At the beginning, 2.5 ppm of EC were used for start-up. Depending on the catalyst and performance, the EC concentration was increased every 24 hours up to a maximum of 7 ppm. The remainder of the feed gas comprised methane. The experiments were carried out at a pressure of 15 bar and a space velocity of gas (GHSV) of 4750/h and a space-time yield of 250 kg of EO/(m3(cat)×h).

The reaction temperature was regulated according to the prescribed ethylene oxide offgas concentration of 2.7%. To optimize the catalyst in respect of selectivity and conversion, from 2.2 to 7.0 ppm of ethylene chloride were added as moderator to the feed gas.

The gas leaving the reactor was analyzed by means of on-line MS. The selectivity was determined from the analytical results.

2. Catalysts Prepared

2.1 Example 1 (not According to the Invention)

140 g of the support A were converted according to general method 1.2-1.5 into the corresponding catalyst. The solution according to general method 1.3 comprised 0.535 g of a 3.1% aqueous rhenium solution produced by dissolving ammonium perrhenate in water.

The catalyst produced comprised 16.7% by weight of silver, tungsten in an amount of 200 ppm by weight, cesium in an amount of 460 ppm by weight, lithium in an amount of 190 ppm by weight and sulfur in an amount of 14 ppm by weight.

The catalyst obtained was tested in accordance with general method 1.6. The result is reported in table 2.

2.2 Example 2 (not According to the Invention)

140 g of the support A were converted according to the general method into the corresponding catalyst. The solution according to general method 1.3 comprised 1.579 g of a 2.1% aqueous rhenium solution produced by dissolving ammonia perrhenate in water.

The catalyst produced comprised 16.5% by weight of silver, tungsten in an amount of 200 ppm by weight, cesium in an amount of 460 ppm by weight, lithium in an amount of 190 ppm by weight and sulfur in an amount of 14 ppm by weight.

The catalyst obtained was tested in accordance with general method 1.6. The result is reported in table 2.

2.3 Example 3 (not According to the Invention)

140 g of the support A were converted according to general method 1.2-1.5 into the corresponding catalyst. The solution according to general method 1.3 comprised 1.659 g of a 3.1% aqueous rhenium solution produced by dissolving ammonium perrhenate in water.

The catalyst produced comprised 16.5% by weight of silver, tungsten in an amount of 200 ppm by weight, cesium in an amount of 460 ppm by weight, lithium in an amount of 190 ppm by weight and sulfur in an amount of 14 ppm by weight.

The catalyst obtained was tested in accordance with general method 1.6. The result is reported in table 2.

2.4 Example 4

140 g of the support A were converted according to general method 1.2-1.5 into the corresponding catalyst. The solution according to general method 1.3 comprised 2.141 g of a 3.1% aqueous rhenium solution produced by dissolving ammonium perrhenate in water.

The catalyst produced comprised 16.5% by weight of silver, tungsten in an amount of 200 ppm by weight, cesium in an amount of 460 ppm by weight, lithium in an amount of 190 ppm by weight and sulfur in an amount of 14 ppm by weight.

The catalyst obtained was tested in accordance with general method 1.6. The result is reported in table 2.

2.5 Example 5

140 g of the support A were converted according to general method 1.2-1.5 into the corresponding catalyst. The solution according to general method 1.3 comprised 2.676 g of a 3.1% aqueous rhenium solution produced by dissolving ammonium perrhenate in water.

The catalyst produced comprised 16.5% by weight of silver, tungsten in an amount of 200 ppm by weight, cesium in an amount of 460 ppm by weight, lithium in an amount of 190 ppm by weight and sulfur in an amount of 14 ppm by weight.

The catalyst obtained was tested in accordance with general method 1.6. The result is reported in table 2.

2.6 Example 6

180 g of the support B were converted according to general method 1.2-1.5 into the corresponding catalyst. The solution according to general method 1.3 comprised 1.637 g of a 4.1% aqueous rhenium solution produced by dissolving ammonium perrhenate in water.

The catalyst produced comprised 16.4% by weight of silver, tungsten in an amount of 200 ppm by weight, cesium in an amount of 420 ppm by weight, lithium in an amount of 190 ppm by weight and sulfur in an amount of 14 ppm by weight.

The catalyst obtained was tested in accordance with general method 1.6. The result is reported in table 2.

2.7 Example 7 (not According to the Invention)

140 g of the support B were converted according to general method 1.2-1.5 into the corresponding catalyst. The solution according to general method 1.3 comprised 1.438 g of a 4.1% aqueous rhenium solution produced by dissolving ammonium perrhenate in water.

The catalyst produced comprised 16.7% by weight of silver, tungsten in an amount of 200 ppm by weight, cesium in an amount of 420 ppm by weight, lithium in an amount of 190 ppm by weight and sulfur in an amount of 14 ppm by weight.

The catalyst obtained was tested in accordance with general method 1.6. The result is reported in table 2.

2.8 Example 8

100 g of the support C were converted according to general method 1.2-1.5 into the corresponding catalyst. The solution according to general method 1.3 comprised 1.185 g of a 3.1% aqueous rhenium solution produced by dissolving ammonium perrhenate in water.

The catalyst produced comprised 15.5% by weight of silver, tungsten in an amount of 200 ppm by weight, cesium in an amount of 350 ppm by weight, lithium in an amount of 190 ppm by weight and sulfur in an amount of 14 ppm by weight.

The catalyst obtained was tested in accordance with general method 1.6. The result is reported in table 2.

2.9 Example 9

220 g of the support C were converted according to general method 1.2-1.5 into the corresponding catalyst. The solution according to general method 1.3 comprised 2.775 g of a 3.1% aqueous rhenium solution produced by dissolving ammonium perrhenate in water.

The catalyst produced comprised 15.5% by weight of silver, tungsten in an amount of 200 ppm by weight, cesium in an amount of 350 ppm by weight, lithium in an amount of 190 ppm by weight and sulfur in an amount of 14 ppm by weight.

The catalyst obtained was tested in accordance with general method 1.6. The result is reported in table 2.

2.10 Example 10 (not According to the Invention)

140 g of the support D were converted according to general method 1.2-1.5 into the corresponding catalyst. The solution according to general method 1.3 comprised 1.254 g of a 4.1% aqueous rhenium solution produced by dissolving ammonium perrhenate in water.

The catalyst produced comprised 15.5% by weight of silver, tungsten in an amount of 200 ppm by weight, cesium in an amount of 350 ppm by weight, lithium in an amount of 190 ppm by weight and sulfur in an amount of 14 ppm by weight.

The catalyst obtained was tested in accordance with general method 1.6. The result is reported in table 2.

2.11 Example 11

120 g of the support D were converted according to general method 1.2-1.5 into the corresponding catalyst. The solution according to general method 1.3 comprised 1.318 g of a 4.1% aqueous rhenium solution produced by dissolving ammonium perrhenate in water.

The catalyst produced comprised 15.5% by weight of silver, tungsten in an amount of 200 ppm by weight, cesium in an amount of 350 ppm by weight, lithium in an amount of 190 ppm by weight and sulfur in an amount of 14 ppm by weight.

The catalyst obtained was tested in accordance with general method 1.6. The result is reported in table 2.

2.12 Example 12

120 g of the support D were converted according to general method 1.2-1.5 into the corresponding catalyst. The solution according to general method 1.3 comprised 1.388 g of a 4.1% aqueous rhenium solution produced by dissolving ammonium perrhenate in water.

The catalyst produced comprised 15.5% by weight of silver, tungsten in an amount of 200 ppm by weight, cesium in an amount of 350 ppm by weight, lithium in an amount of 190 ppm by weight and sulfur in an amount of 14 ppm by weight.

The catalyst obtained was tested in accordance with general method 1.6. The result is reported in table 2.

TABLE 2

| Example | Support [mm] | Re concentration, absolute [ppm] | Re conc. [ppm/mm] | Temperature [° C., 190 h] | Selectivity [%, 190 h] |
| --- | --- | --- | --- | --- | --- |
| 1* | A | 100 | 38.6 | 231.5 | 81.9 |
| 2* | A | 200 | 77.2 | 232.5 | 83.5 |
| 3* | A | 310 | 119.7 | 231.0 | 85.0 |
| 4 | A | 400 | 154.4 | 238.4 | 89.8 |
| 5 | A | 500 | 193.1 | 241.3 | 89.8 |
| 6 | B | 310 | 178.1 | 242.1 | 89.8 |
| 7* | B | 350 | 201.1 | 248.6 | 88.9 |
| 8 | C | 310 | 174.2 | 240.2 | 89.6 |
| 9 | C | 330 | 185.4 | 240.2 | 89.6 |
| 10* | D | 310 | 114.4 | 241.6 | 88.9 |
| 11 | D | 380 | 140.2 | 243.1 | 90.5 |
| 12 | D | 400 | 147.6 | 243.1 | 90.5 |

The supports marked with * are comparative examples

The catalysts marked by * did not achieve the desired maximum performance. The test using the catalysts based on alumina supports having different ring geometries shows that when the alumina support geometry is changed from 6×6×3 [mm×mm×mm] to 8×8×3 [mm×mm×mm] rings (with otherwise identical alumina support properties), the rhenium concentration had to be increased in order to achieve comparable catalytic properties.

The invention claimed is:
1. A shaped catalyst body for preparing ethylene oxide, which comprises at least silver and rhenium applied to an alumina support, wherein the alumina support has the geometry of a hollow cylinder and the shaped catalyst body has a rhenium content $C_R$, and wherein $C_R$/ppm by weight, based on the wall thickness of the hollow cylinder dw in mm, is in the range from $140 \leq C_R/d_w \leq 195$, wherein the hollow cylinder has a length L in the range from 5 to 10 mm, an external diameter $d_A$ in the range from 5 to 10 mm and a ratio of external diameter $d_A$ in mm to the wall thickness $d_W$ in mm in the range from 2.5 to 4.5.

2. The shaped catalyst body according to claim 1, wherein the hollow cylinder has a length L in the range from 6 to 9.5 mm.

3. The shaped catalyst body according to claim 1, wherein the shaped catalyst body comprises silver in an amount of from 5 to 30% by weight, based on the total weight of the shaped catalyst body and calculated as element.

4. The shaped catalyst body according to claim 1, wherein the alumina support has a bimodal pore distribution.

5. The shaped catalyst body according to claim 1, wherein the alumina support has a BET surface area in the range from 0.7 to 1.2 m²/g.

6. The shaped catalyst body according to claim 1, wherein the catalyst comprises at least one promoter selected from the group consisting of elements of groups IA, VIB, VIIB and VIA.

7. The shaped catalyst body according to claim 1, wherein the shaped catalyst body comprises tungsten in an amount in the range from 5 ppm by weight to 500 ppm by weight, cesium in an amount in the range from 100 ppm by weight to 800 ppm by weight, lithium in an amount in the range from 10 ppm by weight to 500 ppm by weight and sulfur in an amount in the range from 0 to 50 ppm by weight, calculated as element and based on the total weight of the shaped catalyst body.

8. A process for producing a shaped catalyst body comprising silver and rhenium applied to an alumina support, which comprises
(a) providing an alumina support which has the geometry of a hollow cylinder,
(b) applying silver and rhenium to the alumina support, with rhenium being applied in an amount of $C_R$/ppm by weight, based on the wall thickness of the hollow cylinder $d_W$ in mm and calculated as element which is in the range $140 \leq C_R/d_w \leq 195$, to the alumina support, wherein the hollow cylinder has a length L in the range from 5 to 10 mm, an external diameter $d_A$ in the range from 5 to 10 mm and a ratio of external diameter $d_A$ in mm to the wall thickness $d_W$ in mm in the range from 2.5 to 4.5.

9. The process according to claim 8, wherein the process further comprises
(c) calcining the alumina support obtained according to (b).

10. The process according to claim 8, wherein silver is applied in an amount of from 5 to 30% by weight, based on the total weight of the shaped catalyst body and calculated as element, in (b).

11. A shaped catalyst body obtainable or obtained by a process according to claim 8.

12. A process for preparing ethylene oxide which comprises gas-phase oxidation of ethylene by means of oxygen in the presence of the shaped catalyst body according to claim 1.

13. The shaped catalyst body according to claim 1, wherein the catalyst comprises at least one promoter selected from the group consisting of tungsten, cesium, lithium and sulfur.

14. The shaped catalyst body according to claim 1, wherein the alumina support is an alpha-alumina support.

15. The shaped catalyst body according to claim 2, wherein the shaped catalyst body comprises silver in an amount of from 5 to 30% by weight, based on the total weight of the shaped catalyst body and calculated as element.

16. The shaped catalyst body according to claim 15, wherein the alpha-alumina support, which has a bimodal pore distribution.

17. The shaped catalyst body according to claim 16, wherein the alpha-alumina support has a BET surface area in the range from 0.7 to 1.2 m²/g.

18. The shaped catalyst body according to claim 17, wherein the catalyst comprises at least one promoter selected from the group consisting of elements of groups IA, VIB, VIIB and VIA.

19. The shaped catalyst body according to claim 18, wherein the shaped catalyst body comprises tungsten in an amount in the range from 5 ppm by weight to 500 ppm by weight, cesium in an amount in the range from 100 ppm by weight to 800 ppm by weight, lithium in an amount in the range from 10 ppm by weight to 500 ppm by weight and sulfur in an amount in the range from 0 to 50 ppm by weight, calculated as element and based on the total weight of the shaped catalyst body.

* * * * *